US009146198B2

(12) United States Patent
Wendler et al.

(10) Patent No.: US 9,146,198 B2
(45) Date of Patent: Sep. 29, 2015

(54) DEVICE AND METHOD FOR COMBINED OPTICAL AND NUCLEAR IMAGE ACQUISITION

(75) Inventors: Thomas Wendler, Munich (DE); Nassir Navab, Munich (DE)

(73) Assignee: SURGICEYE GMBH, Munich (DE)

( * ) Notice: Subject to any disclaimer, the term of this patent is extended or adjusted under 35 U.S.C. 154(b) by 248 days.

(21) Appl. No.: 13/806,403

(22) PCT Filed: Jun. 22, 2011

(86) PCT No.: PCT/EP2011/060519
§ 371 (c)(1),
(2), (4) Date: Mar. 14, 2013

(87) PCT Pub. No.: WO2011/161197
PCT Pub. Date: Dec. 29, 2011

(65) Prior Publication Data
US 2013/0168570 A1 Jul. 4, 2013

(30) Foreign Application Priority Data

Jun. 23, 2010 (DE) .......................... 10 2010 017 543

(51) Int. Cl.
*G01N 23/00* (2006.01)
*H01L 27/146* (2006.01)
*A61B 5/00* (2006.01)
(Continued)

(52) U.S. Cl.
CPC .............. *G01N 23/00* (2013.01); *A61B 5/0059* (2013.01); *A61B 6/037* (2013.01); *A61B 6/4417* (2013.01);
(Continued)

(58) Field of Classification Search
CPC .............................. G01N 23/00; H01L 27/146
USPC .............................................. 250/395, 336.1
See application file for complete search history.

(56) References Cited

U.S. PATENT DOCUMENTS

2006/0108509 A1 5/2006 Frangioni et al.
2008/0317313 A1 12/2008 Goddard et al.

FOREIGN PATENT DOCUMENTS

EP           01916543 A1    4/2008
WO     WO-03/104799 A2    12/2003

OTHER PUBLICATIONS

Peter, J., et al.: "Development and Initial Results of a Dual-Modality Spect/Optical Small Animal Imager", Nuclear Science Symposium Conference Record, 2005 IEEE Wyndham El Conquistador Resort, Puerto Rico Oct. 23-29, 2005, Piscataway, NJ, USA, IEEE, Bd. 4, Oct. 23, 2005, Seiten 1969-1972, XP010895979, DOI: 10.1109/NSSMIC.2005.1596718; ISBN: 978-0-7803-9221-2.
International Search Report in PCT/EP2011/060519, Sep. 2, 2011.

*Primary Examiner* — David Porta
*Assistant Examiner* — Faye Boosalis
(74) *Attorney, Agent, or Firm* — Patterson & Sheridan, LLP

(57) ABSTRACT

A device for combined optical and nuclear image comprises a nuclear image acquisition module and a reference image acquisition module. The reference image acquisition module has: an optical image sensor; and an optical imaging system for deflecting the optical radiation from a reference field of view to the image sensor, wherein the optical imaging system comprises a mirror for the optical radiation, which mirror is arranged between the reference field of view and the optical image sensor. On the image sensor, a respective image area assigned to at least one of nuclear partial fields of view. The optical imaging system is arranged such that the optical radiation coming from the at least one nuclear partial field of view is deflected substantially exactly to the respectively assigned of the image areas.

13 Claims, 8 Drawing Sheets

(51) Int. Cl.
*A61B 6/03* (2006.01)
*A61B 6/00* (2006.01)
*G01N 21/00* (2006.01)
*G01T 1/16* (2006.01)

(52) U.S. Cl.
CPC ............. *A61B 6/4429* (2013.01); *A61B 6/5247* (2013.01); *A61B 6/583* (2013.01); *G01N 21/00* (2013.01); *G01T 1/1603* (2013.01); *H01L 27/146* (2013.01)

DEVICE AND METHOD FOR COMBINED OPTICAL AND NUCLEAR IMAGE ACQUISITION

BACKGROUND

1. Field

The invention lies in the field of image acquisition and specifically in particular combined optical and nuclear image acquisition, and relates to a device for such image acquisition.

2. Description of Related Art

Nuclear imaging methods have proved extremely useful in various fields, in particular in nuclear medical fields and in the search for radioactively contaminated material such as nuclear waste. In nuclear imaging methods the nuclear radiation coming from a spatial region is visualized in a two- or three-dimensional image and thus made perceptible for humans. The spatial region in which the spatial distribution of the nuclear radiation can be sufficiently reliably detected is also designated as nuclear field of view. In cases in which the boundaries of this spatial region are fluid, the nuclear field of view can be defined appropriately, for example, by a predefined sensitivity threshold for the radiation intensity and/or for the spatial resolution of the detector: the nuclear field of view is then the spatial region whose radiation can be detected by the detector having a sensitivity exceeding the sensitivity threshold.

Despite their appreciable benefit, the evaluation of the generated nuclear images is difficult. This is also because the structures identifiable in the nuclear image cannot easily be assigned to the structures perceptible with the naked eye. Thus, for example no anatomical structures are visible in a typical medical nuclear image.

This problem can be ameliorated by applying radioactive markers to known anatomical positions. The markers can then be detected in the nuclear image in order to obtain at least coarse reference points. Systems for hybrid SPECT/CT or PET/CT recording are known in order to superpose CT images containing anatomical information with nuclear images. At the present time, methods are also being developed to represent three-dimensional nuclear images in suitable perspective and superpose with a video image in order to jointly detect anatomical and nuclear image information in this way.

Apparatus for the combined detection of x-ray and optical images are also known, possibly from DE 10049103, JP 61057804, US 2007/0019787, U.S. Pat. Nos. 6,447,163 and 3,679,901. However, the approaches used there cannot easily be applied to the visualization of nuclear radiation since the x-ray and nuclear imaging methods are based on different basic principles. In US 2007/0019787, the x-ray and optical images must additionally be recorded in a time-offset manner. Moving samples cannot therefore be optimally detected.

EP 0 743 538 describes a device for the remote localization of radioactive sources in an observation zone. The apparatus has a mirror and an optical camera for supplying an image of the observation zone and means for detecting radioactive rays. The means for detecting radioactive rays comprises a collimator having a single collimator opening (pinhole collimator) which allows the recording of a spatially resolved nuclear images. The nuclear image can then be combined with the image of the optical camera, However, the attainable image quality of the nuclear image is restricted by the pinhole collimator in a certain time frame.

BRIEF SUMMARY

Against this background, a device for combined optical and nuclear image acquisition according to claim 1 and a method for image acquisition according to claim 13 is proposed. Further advantages, features, aspects and details of the invention and preferred embodiments and particular aspects of the invention are obtained from the subclaims, the description and the figures.

The invention lies in the field of image acquisition and specifically in particular combined optical and nuclear image acquisition, and relates to a device for such image acquisition, in particular such a device having a nuclear image acquisition module for detecting an intensity distribution of nuclear radiation and a reference image acquisition module for detecting an intensity distribution of optical radiation. The invention further relates to a method for image acquisition.

BRIEF DESCRIPTION OF THE DRAWINGS

The invention will be explained in detail hereinafter with reference to exemplary embodiments shown in the following figures from which further advantages and modifications are obtained.

Figure 1:
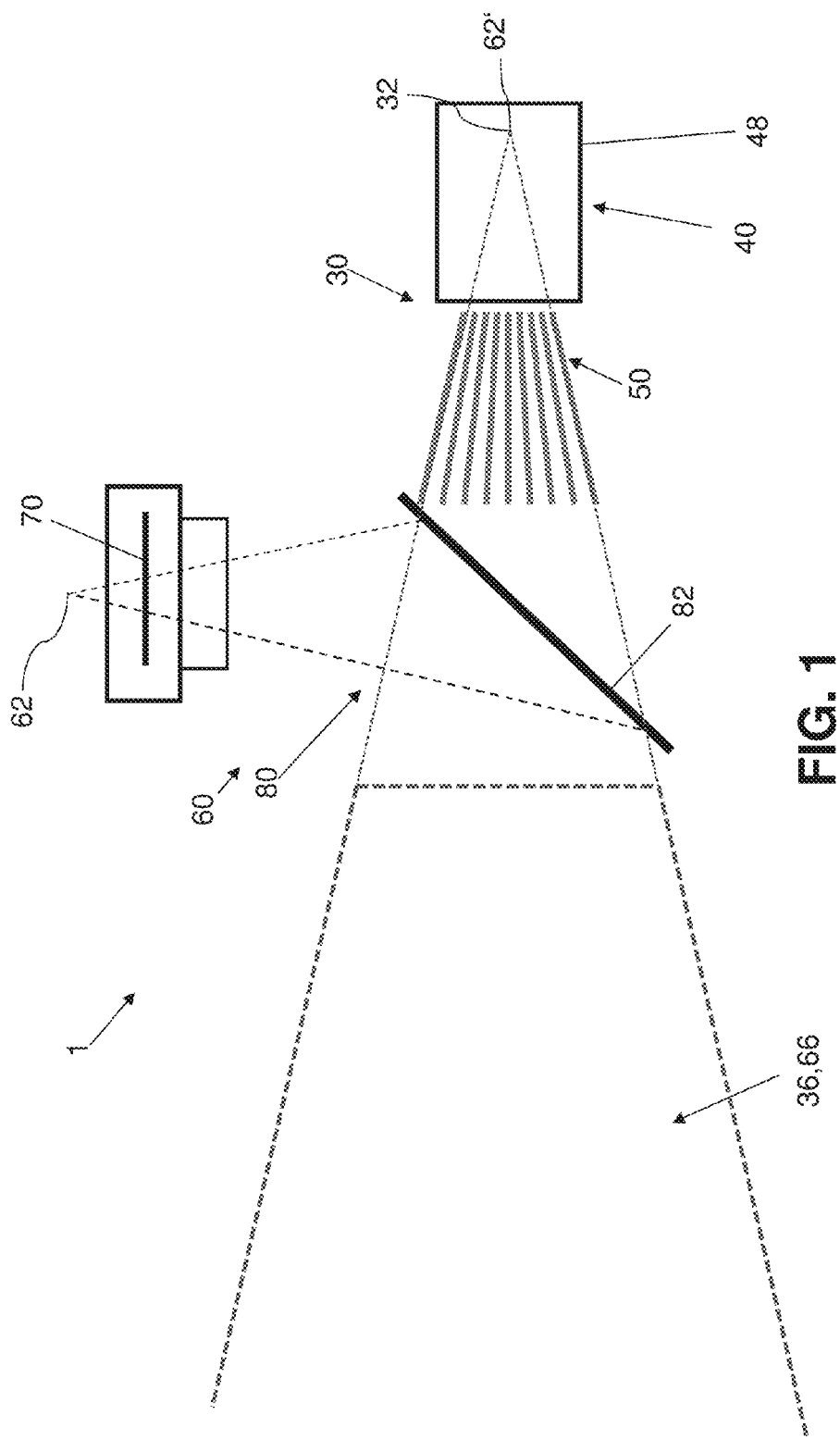
FIG. 1 shows a schematic side view of a device according to a first embodiment of the invention.

In the figures, elements which are similar or correspond to one another are characterized by the same reference numbers. Individual aspects and properties described herein, even when they are described in connection with individual embodiments, can be combined arbitrarily with other aspects, properties or embodiments in order to obtain further embodiments.

DETAILED DESCRIPTION

According to one aspect of the invention, a device for combined optical and nuclear image acquisition is proposed. The device comprises one, therefore at least one, nuclear image acquisition module; and a reference image acquisition module. The nuclear image acquisition module is adapted for detecting an intensity distribution of nuclear radiation coming from a nuclear field of view, i.e. information as to whether and optionally how many nuclear radiation particles were detected per location. The nuclear image acquisition modules comprise a nuclear radiation detector and a collimator arranged between the nuclear field of view and the nuclear radiation detector having a plurality of collimator openings, wherein the, or even each, of the collimator openings are arranged for transmission of partial radiation of the nuclear radiation coming from a respective nuclear partial field of view of the nuclear field of view. The reference image acquisition module is adapted for detecting an intensity distribution of optical radiation coming from a reference field of view and comprises: an optical image sensor; and an optical imaging system for deflecting the optical radiation from the reference field of view to the image sensor, wherein the optical imaging system (relative to the beam path) comprises a mirror for the optical radiation arranged between the reference field of view and the optical image sensor. On the image sensor a respective image area is assigned to at least one, to a plurality of, or even to each of the nuclear partial fields of view, and specifically the assignment is made by the optical imaging system and its arrangement: the optical imaging system is arranged to deflect the optical radiation coming from a respective one of the at least one nuclear partial fields of view or even from each of the nuclear partial fields of view substantially exactly to the respectively assigned one of the image areas. Accordingly the imaging system is tuned to the collimator and the plurality of collimator openings.

In particular, thanks to the plurality of collimator openings, it is possible to record a high-quality spatially resolved nuclear image. In addition, the optical imaging system makes it possible to assign an optical image to the nuclear image in a simple manner and in real time. The assignment can be carried out correctly for different spatial depths, i.e. in three dimensions, since the nuclear partial fields of view including their image depth are assigned to the respective fields of view of the optical image sensor.

The optical camera can comprise a laparoscope, endoscope, one or more general cameras or the like. Also cameras which can only record narrow (narrow-band) and/or a plurality of separate frequency bands, e.g. multispectral cameras or which themselves emit light for image acquisition such as fluorescence cameras, interference cameras or time-of-flight cameras can also be used as optical cameras. Optical radiation is understood as any electromagnetic radiation which can be deflected by a mirror. This is usually possible in a wavelength range between 100 nm and 10 µm. The mirror is accordingly suitable for reflecting at least an appreciable part of the optical radiation but can be transmitting for nuclear radiation. The nuclear radiation can, for example, comprise neutrons, alpha, beta and/or gamma rays having, for example, more than 15 keV. Accordingly, the nuclear radiation detector can be a gamma, beta, Compton detector. The nuclear radiation detector can also comprise another nuclear radiation detector opposite the nuclear field of view in order, for example, to detect low-noise PET signals.

According to a further aspect of the invention, the device can be advantageously used for medical imaging, in particular for nuclear guided surgery, nuclear medicine and cell detection; additionally the invention can also be used for the detection of radioactive waste.

The invention also relates to a device for carrying out the disclosed method and also comprises device parts for executing individual process steps. These process steps can be executed by hardware components, by a computer programmed by means of corresponding software, by a combination of both or in some other manner. The invention is further directed towards a method according to which the devices described in each case operate. It includes process steps for executing each function of the devices.

FIG. 1 serves to illustrate some general aspects of the invention which are explained in the following. FIG. 1 shows a device 1 for combined optical and nuclear image acquisition according to one embodiment of the invention. The device 1 has a nuclear image acquisition module 30 and a reference image acquisition module 60. The nuclear image acquisition module 30 has a collimator 50 and a nuclear radiation detector 40 which, for example, can be the nuclear radiation detector shown more accurately in FIG. 2. The reference image acquisition module 60 comprises an optical image sensor 70 and an optical imaging system 80 with a mirror 82 which reflects optical radiation but is transparent for nuclear radiation.

The collimator 50 has a plurality of collimator openings and is designed as a diverging holes collimator: the collimator openings are directed away from a common approximately point-like centre 32 and towards a nuclear field of view 36. The centre 32 is typically designated as perspective nuclear radiation centre 32. For a sufficiently long collimator 50, this geometry of the collimator 50 allows a perspective spatially resolved nuclear radiation image of the nuclear radiation in the nuclear field of view 36 to be obtained through the detector 40; namely, each of the collimator openings defines a partial field of view of the nuclear field of view 36 directed towards the centre 32 so that the detector 40 detects the radiation coming from the corresponding partial field of view in a corresponding image area of the nuclear radiation image. As a result, a spatially resolved perspective nuclear image with perspective centre 32 is produced. Accordingly, the nuclear field of view 36 overall has a lateral boundary directed substantially towards the centre 32. For a finite collimator length, such a perspective image is generated at least approximately.

The optical imaging system 80 is arranged to deflect optical radiation from the reference field of view 66 to the image sensor 70. The optical imaging system 80 is also adapted to produce a perspective image, i.e. the optical radiation is thus deflected from the reference field of view 66 to the image sensor 70 so that optical radiation coming from respective partial volumes running towards a virtual optical centre 62' is deflected onto respective image areas of the image sensor. The position of the centre 62' is predefined by the non-reflected perspective centre 62 and the mirror 82. The non-reflected perspective centre 62 is in turn predefined by a camera optics (comprising lenses and aperture) pertaining to the image sensor 70 and optionally other optical elements. In FIG. 1 the non-reflected perspective centre 62 is located behind the image sensor 70 but depending on optical elements, can also lie in front of the image sensor 70. The reference field of view 66 has a lateral boundary directed substantially towards the virtual optical centre 62'. FIG. 1 shows a randomly selected front boundary of the reference field of view or of the nuclear field of view. Likewise a rear boundary can be given. These boundaries can, for example, be determined by the accessibility of the measurement space, the sensitivity of the nuclear radiation detector 40 and the like. Herein a boundary is substantially understood as the lateral boundary in the region lying in front of the outermost mirror or other optical element.

In FIG. 1 the position and orientation of the image sensor 70, the mirror 82 and optionally other optical elements is selected so that the position of the virtual optical centre 62' coincides substantially with the position of the nuclear image centre 32. In order to achieve a congruent position of the two centres 32, 62', it is to be provided in particular that the (real) centre 62 and the centre 32 have the same distance from a centre of the mirror 82. Due to the coincidence of the centres 32, 62', the reference image acquisition module 60 can detect an optical image having the same perspective as a nuclear image detected by the nuclear image acquisition module 30. The joint perspective allows a good spatial assignment of the nuclear image with the optical image in the entire spatial region within the reference field of view or the nuclear field of view. In FIG. 1 the nuclear field of view 36 and the reference field of view 66 are even selected to be the same. However, this is not a necessary condition. For example, the nuclear field of view 36 could be contained in the reference field of view 66 or conversely or nuclear field of view 36 and reference field of view 66 overlap in a different manner.

Figure 2:
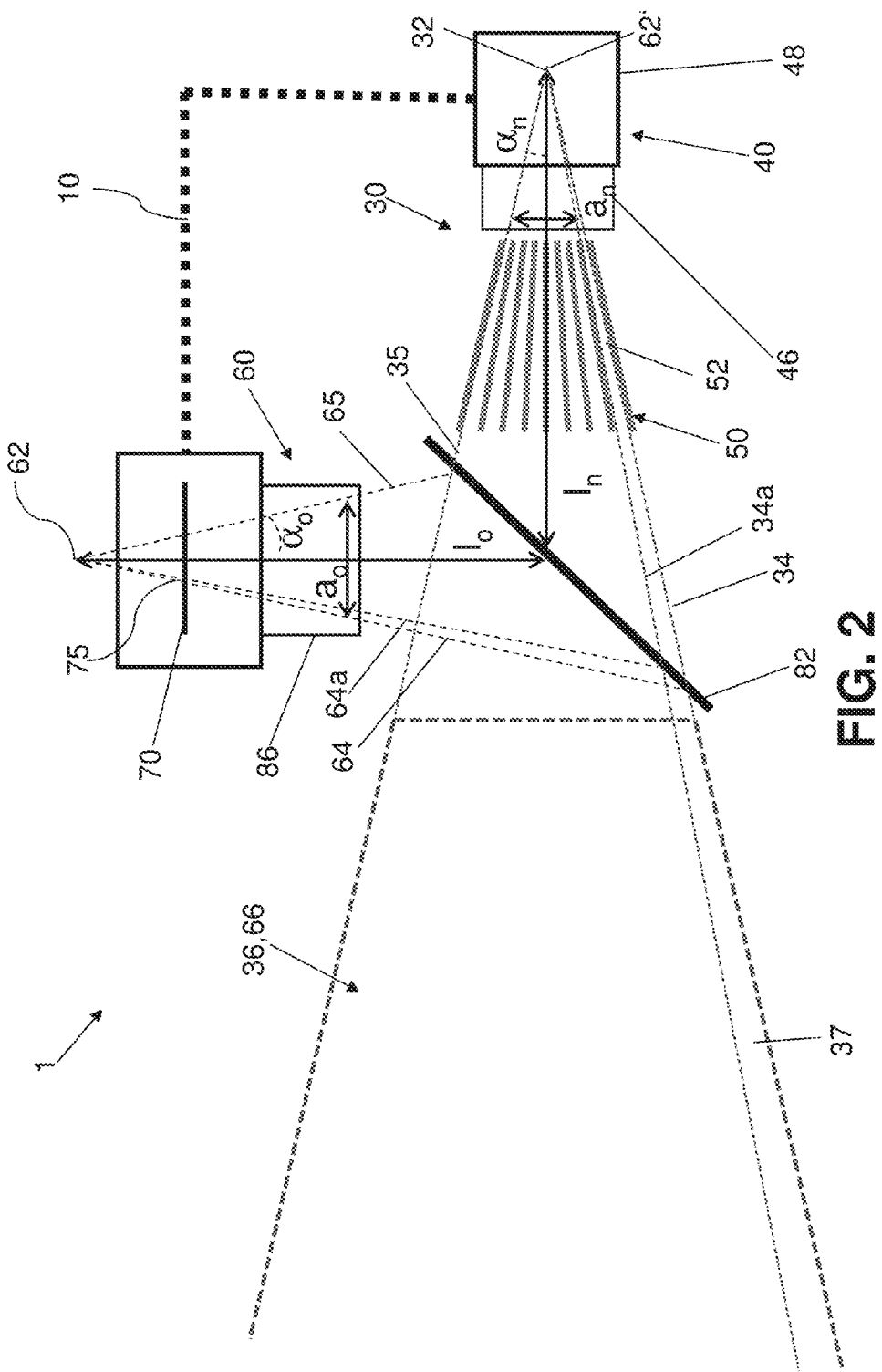
FIGS. 2-6 show respective schematic side views of a device according to a second to sixth embodiment of the invention.

FIG. 2 shows a similar device to that shown in FIG. 1 with some further details. The description of FIG. 1 applies accordingly also to FIG. 2 and only the further details will be described hereinafter. FIG. 2 shows further details of the nuclear radiation detector 40 which comprises a scintillator 46 and an array of photodiodes 48. The collimator 50 is arranged in the beam direction ahead of the scintillator 46 and has a plurality of collimator openings 52. As further details of the reference image acquisition module 60, in addition to the optical image sensor 70 a lens arrangement 86 is also shown. The lens arrangement determines the position of the non-reflected perspective centre 62. In addition, lateral boundaries 34, 35 of the nuclear field of view 36 and lateral boundaries 64, 65 of the optical reference field of view 66 are shown.

Furthermore, for one of the collimator openings 52 of the collimator 50, FIG. 2 shows as an example the corresponding partial field of view 37, laterally delimited by the boundaries 34, 34a. The collimator opening 52 is arranged so that it transmits the nuclear radiation coming from the nuclear partial field of view 37. A corresponding image area of the scintillator 46 is assigned to the collimator opening 52 or the partial field of view 37 so that the scintillator 46 and therefore the detector 40 detects the radiation coming from the partial field of view 37 in this image area. Since the remaining collimator openings are configured in a corresponding manner, overall a spatially resolved perspective nuclear image with perspective centre 32 and a resolution predefined by the collimator 50 is produced. In this description a lack of sharpness of the nuclear image as a result of the finite length of the collimator is neglected. This neglect will be retained in the following. In particular, if specific relations are therefore described as "substantially" in the following, this should include a neglect of such lack of sharpness.

Due to the coincidence of the nuclear radiation centre 32 and the virtual optical centre 62', the reference image acquisition module 60 can detect an optical image having the same perspective as the nuclear image acquisition module 30. There is therefore an optical partial field of view corresponding to the nuclear partial field of view 37, namely the partial field of view delimited by the lateral boundaries 64 and 64a. The optical radiation coming from the optical partial field of view is detected on an image area 75 of the optical image sensor 70. Consequently, the image area 75 is assigned to the nuclear partial field of view 37. This assignment is substantially accomplished by the optical imaging system 80 and its arrangement: the optical imaging system 80 is arranged in order to deflect the optical radiation coming substantially from the nuclear partial field of view 37 precisely to the image area 75.

In order that the centres 32 and 62' coincide, it is expedient that the distance $l_o$ of the optical centre 62 from the centre of the mirror 82 and the distance $l_n$ of the nuclear radiation centre 32 from the centre of the mirror 82 are the same. Furthermore, it is expedient that the aperture $\alpha_o$ or the angle $\alpha_o$ of the optical image sensor 70 or the appurtenant optical arrangement 86 is larger than or the same as the aperture $a_n$ predefined by the collimator 50 (relative to the same distance from the centre 32 as the aperture $a_o$) or the angle $\alpha_n$. In FIG. 2 the apertures or angles are selected to be the same so that nuclear field of view 36 and reference field of view 66 are the same.

Furthermore FIG. 2 shows schematically an optional rigid frame 10. The frame 10 connects the optical image sensor 70 and the nuclear radiation detector 40 rigidly to one another. The rigid connection does not exclude the fact that the optical image sensor 70 and the nuclear radiation detector 40 are movable with respect to one another possibly by calibrating, aligning elements or the like. However, the frame 10 allows a rigid and reliable connection at least during operation. Consequently, the assignment between the image area 75 and the nuclear partial field of view 37 is reliably ensured. The mirror 82 and further optical elements can be rigidly connected to the frame 10.

Figure 3:
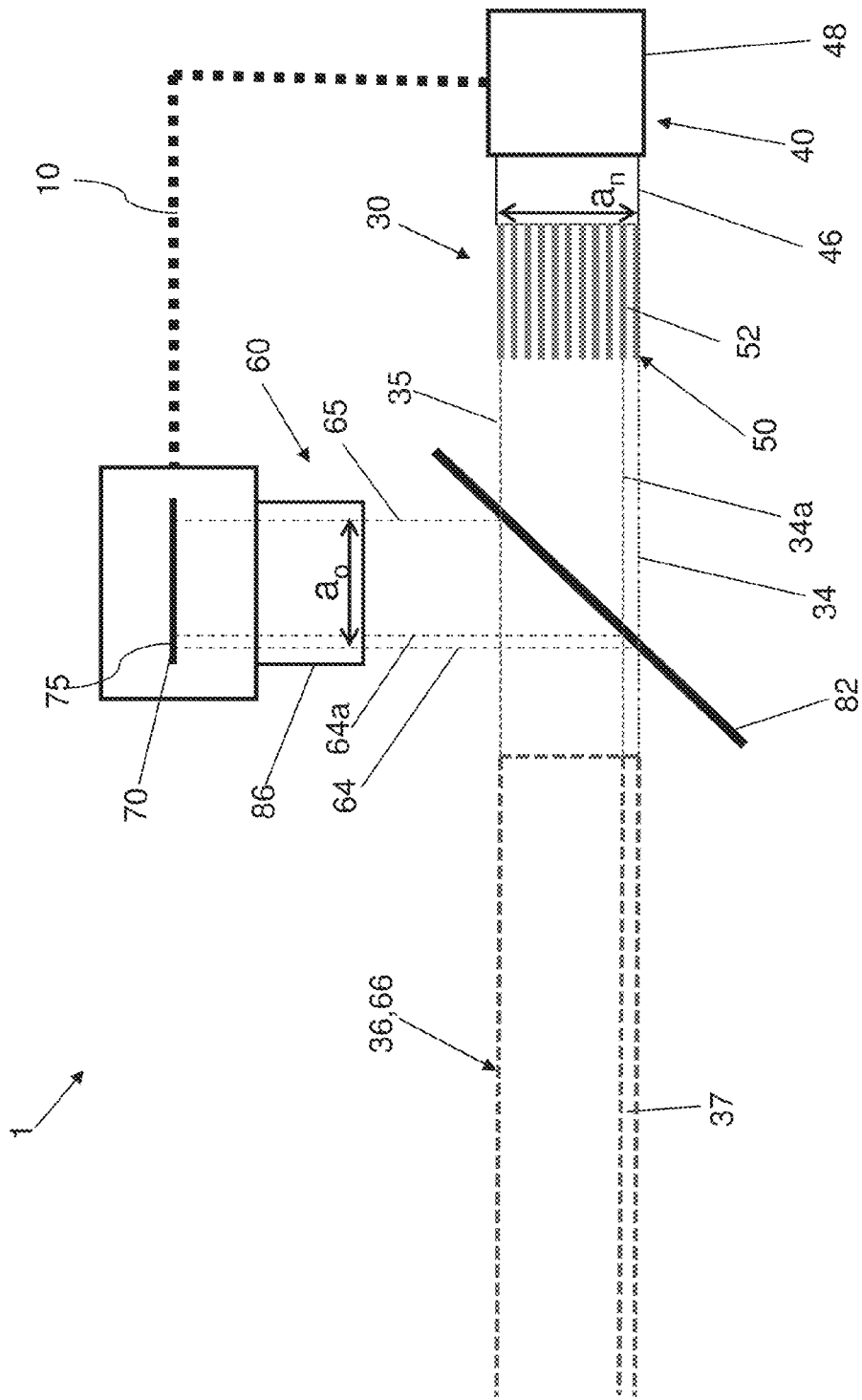

FIG. 3 shows an embodiment similar to FIG. 2. Apart from the differences described hereinbelow, the description of the FIGS. 1 and 2 also applies to FIG. 3. In contrast to FIG. 2, in FIG. 3 the collimator 50 has parallel openings 52. A perspective centre 32 as in FIG. 2 therefore does not exist or is shifted to infinity. The nuclear partial fields of view 37 defined by the respective collimator openings 52 run parallel to one another and substantially, i.e. neglecting the finite collimator length, do not widen. Consequently, the nuclear image acquisition module 30 from FIG. 3 does not have perspective but telecentric imaging properties.

Accordingly, the reference image acquisition module 60 or the optical imaging system 80 has telecentric imaging properties so that the optical radiation coming from the nuclear partial fields of view 37 is deflected substantially precisely to a respectively assigned one of the image areas 75, as described for FIG. 2. The telecentric imaging properties of the optical imaging system 80 can be achieved, for example, by means of a telecentric objective lens. Alternatively, a collimator for optical radiation having a spatially resolved optical detector 70 located behind it can be used to achieve the telecentric imaging properties in the same way as the nuclear image acquisition module. A CCD camera (possibly without further objective optics) or an array of low-sensitivity photodiodes possibly come into consideration as a spatially resolved optical detector 70. In this case, an array of optical fibres can guide the light from one end of the optical collimator to the optical detector.

Figure 4:
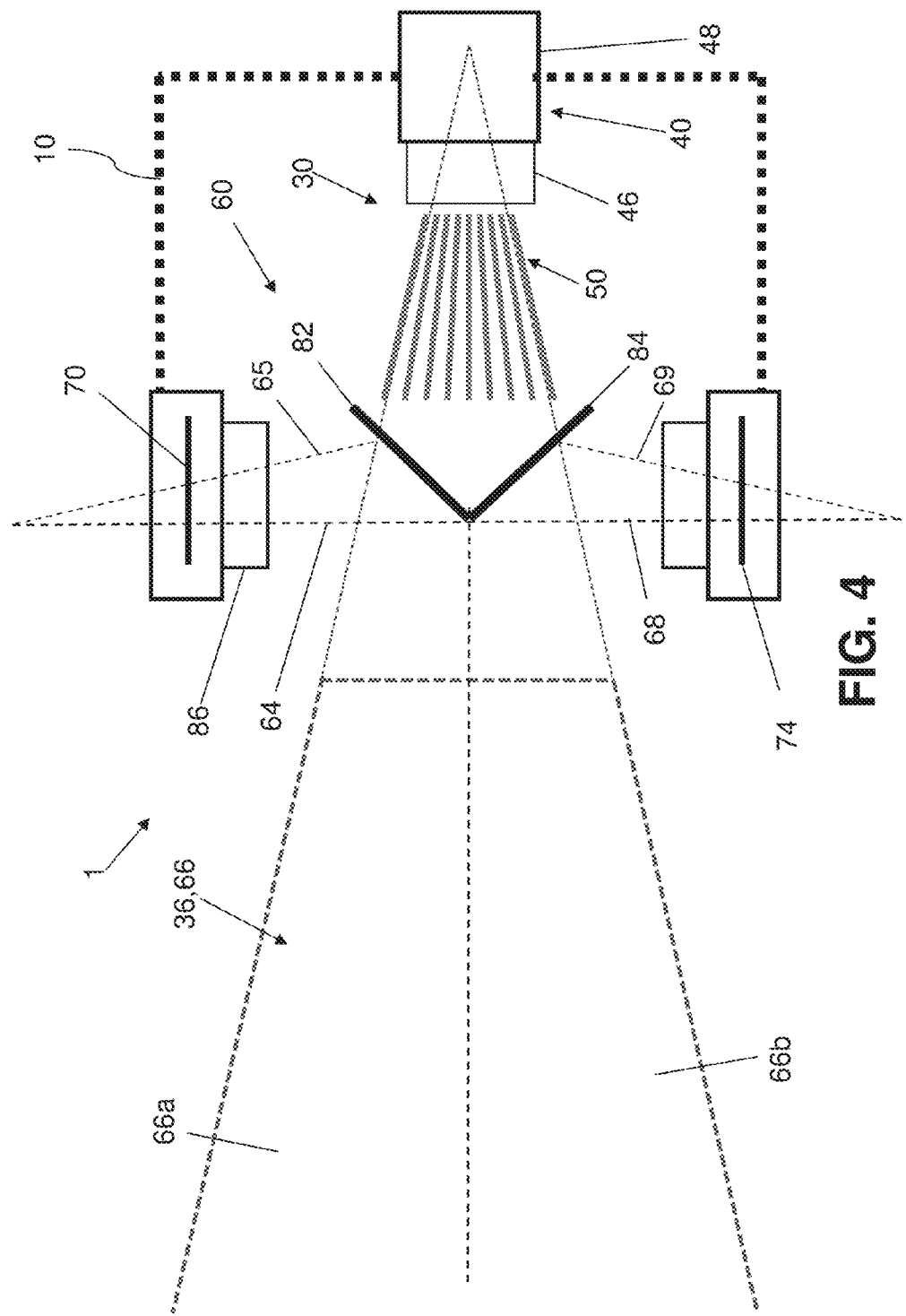

FIG. 4 shows another modification of the embodiment shown in FIG. 2. Again, apart from the differences described hereinbelow, the description of FIGS. 1 and 2 also applies accordingly to FIG. 4. In FIG. 4, apart from the (first) image sensor 70, the reference image acquisition module also comprises a second image sensor 74 and the optical imaging system 80 comprises, in addition to the (first) mirror 82 a second mirror 84. The optical field of view of the first image sensor 70 is laterally delimited by the lines 64, 65 and the first mirror 82 is arranged to reflect this field of view 66a so that it covers one (the upper) part of the nuclear field of view 36. The optical field of view of the second image sensor 74 is laterally delimited by the lines 68, 69 and the mirror 84 is arranged in order to reflect this field of view 66b so that it covers another (the lower) part of the nuclear field of view 36. The fields of view 66a and 66b jointly form the field of view 66 of the reference image acquisition module. In FIG. 4 the field of view 66 of the reference image acquisition module is substantially the same as the nuclear radiation field of view 36. However, the field of view 66 can however also only overlap the nuclear radiation field of view 36. Along with the first image sensor 70 and the nuclear radiation detector 40, the rigid frame 10 is also rigidly connected to the second image sensor 74 and the mirrors 82, 84.

Consequently, the second mirror 82 deflects the optical radiation from the reference field of view 66, more accurately from the part 66a of the reference field of view 66, to the second image sensor 74. Similarly as already described for FIGS. 1 and 2, the virtual centres of the image sensors 70, 74 and the perspective centre of the collimator 50 in FIG. 4 also agree. As a result of the coincidence of the centres, the optical images detected by the image sensors 70, 74 have the same perspective as the nuclear image detected by the nuclear image acquisition module 30. This in turn enables a good spatial assignment of the nuclear image with the respective optical images or with a combined optical image of the image sensors 70 and 74.

Figure 5:
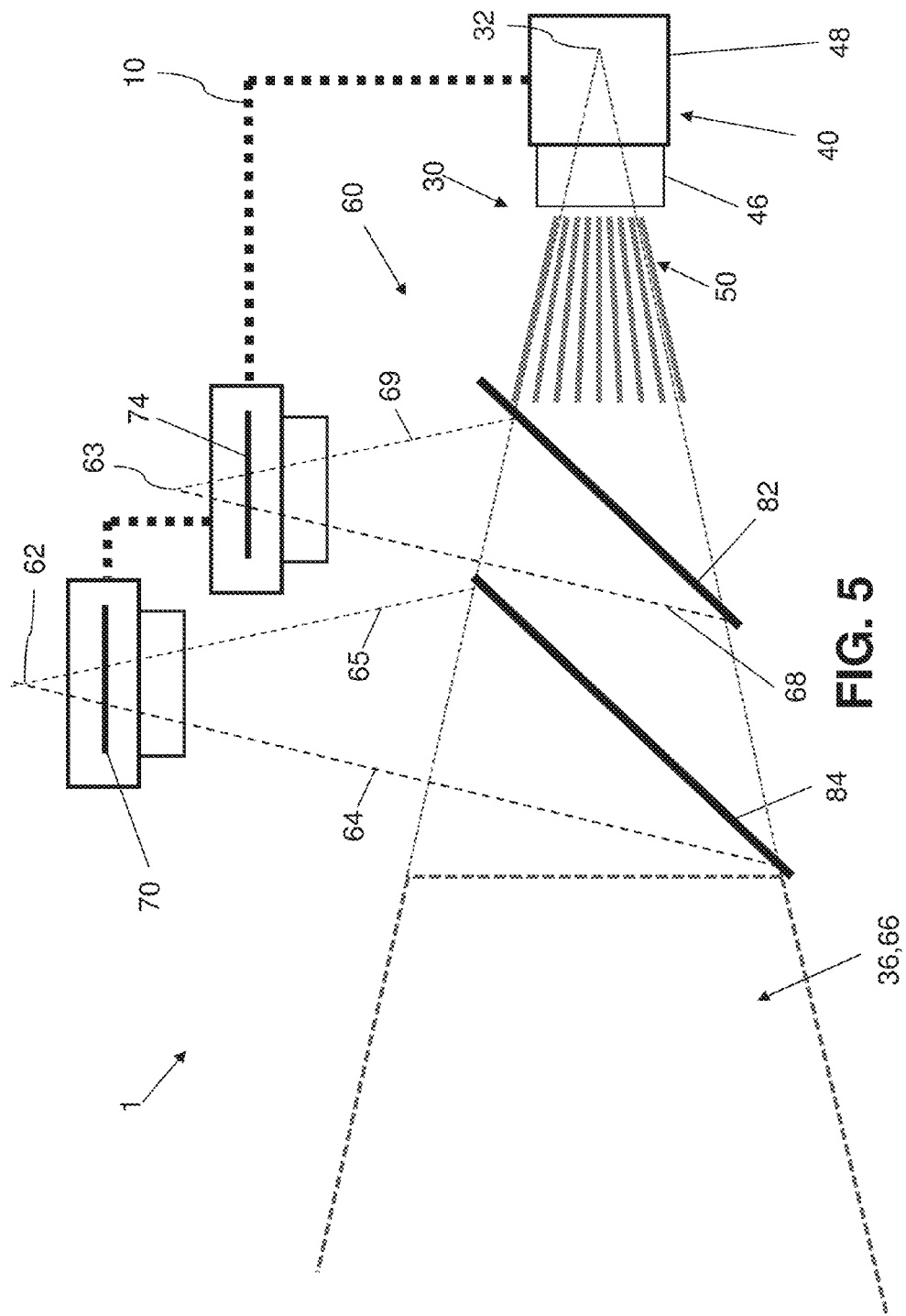

A device 1 with two image sensors 70, 74 is also shown in FIG. 5 and the description of FIGS. 1, 2 and 4 applies accordingly for FIG. 5 apart from the differences described in the following. The first image sensor 70 and the first mirror 82 are arranged as shown in FIGS. 1 and 2. The first image sensor 70 is adapted to detect optical radiation of a first type, e.g. of a first polarisation or of a first wavelength range. The first mirror 82 is adapted to reflect the optical radiation of the first type as described in FIGS. 1 and 2. The second mirror 84 is adapted to reflect optical radiation of the second kind as described in FIGS. 1 and 2 but to transmit the optical radiation of the first type. In FIG. 5 the respective virtual centres of the image sensors 70, 74 and the perspective centre of the collimator 50 agree. As a result of the coincidence of the centres, the optical images detected by the image sensors 70, 74 and the nuclear image detected by the nuclear image acquisition module 30 have a single common perspective. This in turn enables a good spatial assignment of the nuclear image and the optical images of the image sensors 70 and 74 between one another. All three images can be superposed with the same spatial assignment to one another. As a result of the possibility of selectively detecting optical radiation of various types, additional information about the reference field of view 66 can be obtained and an optical image with improved contrast can be obtained.

Figure 6:
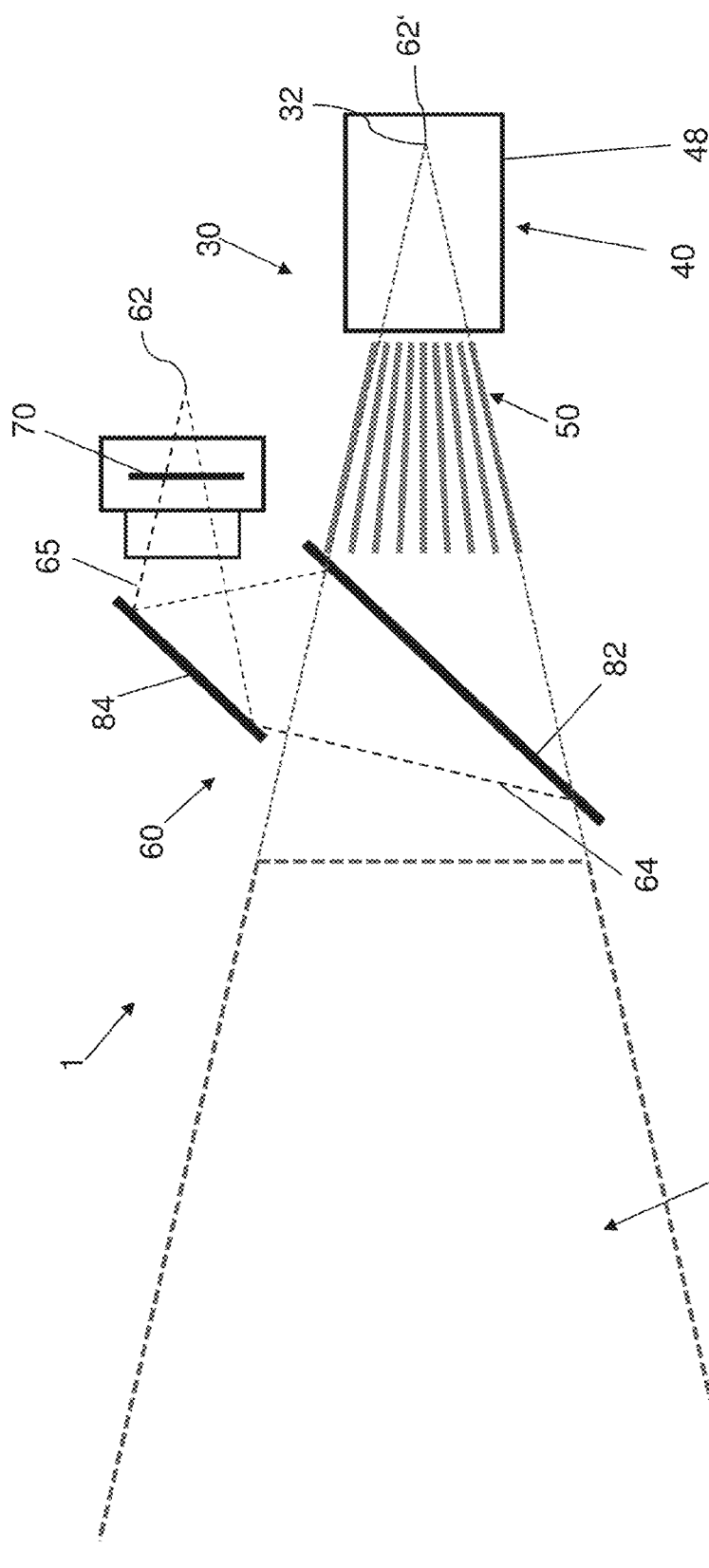

FIG. 6 shows a device for which the description of FIGS. 1 and 2 again applies accordingly apart from the differences described in the following. In FIG. 6, instead of a single mirror 82, an arrangement comprising several mirrors 82, 84 is shown. The optical radiation coming from the reference field of view 66 is initially reflected by the mirror 82 and then reflected by the mirror 84 to the image sensor 70. The position and orientation of the mirrors 82, 84 and optionally other optical elements is selected so that the position of the virtual optical centre 62' substantially coincides with the position of the nuclear image centre 32. Due to the additional mirror 84, the position of the image sensor 70 can be selected more freely and therefore a more compact arrangement of the elements of the reference image acquisition module 60 can be achieved overall.

The devices shown in FIGS. 1 to 6 can be varied still further. For example, in some of the devices shown only a collimator with diverging openings is shown. However, a collimator with parallel openings is also possible. In this case, the reference image acquisition module 60 has accordingly adapted telecentric imaging properties as described with reference to FIG. 3. Furthermore, a different opening geometry of the collimator can also be selected, e.g. multipinhole collimators, converging collimators, aperture coded collimators, etc. and in this case, the imaging properties of the reference image acquisition module 60 can be adapted accordingly so that the optical radiation coming from a respective one of the nuclear partial fields of view is deflected substantially precisely to a respectively assigned image area of the optical image sensor 70.

Figure 7:
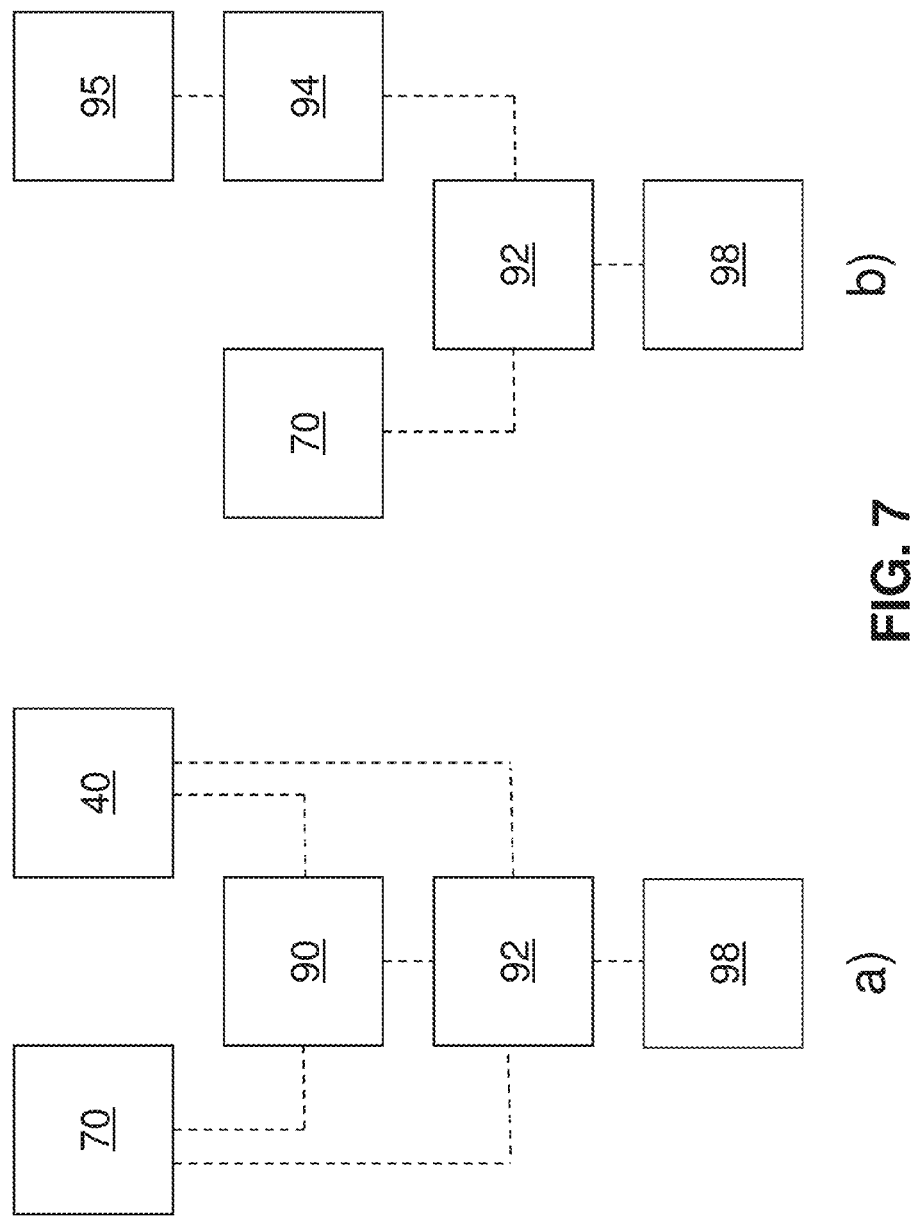
FIG. 7a shows schematic diagrams of further embodiments with modules for image calibration and generation.

FIG. 7a shows a further embodiment with a module for image calibration and generation. A calibrating module 90 is connected to the image sensor 70 and the nuclear radiation detector 40. The calibrating module 90 allows the assignment of spatially the same image coordinates of a nuclear radiation image detected by the nuclear radiation detector 40 and an optical image detected by the image sensor 70. In the simplest case, the calibrating module can simply comprise for example, a table or calculation specification generated during the manufacture of the device, which makes this assignment. In other embodiments, however, it is desirable to allow such an assignment by the user. For this case the calibrating module can comprise a calibrating routine which can be performed by the user. Such a calibrating routine is shown in the following with reference to FIGS. 8a and 8b.

Figure 8:
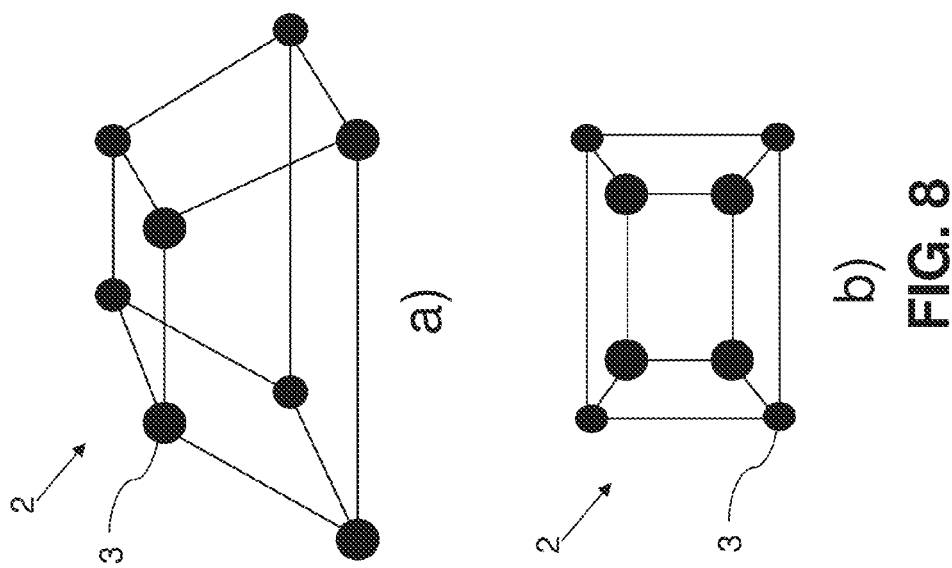
FIG. 8a shows a perspective view of a calibrating element and FIG. 8b show an image of this calibrating element generated by the device.

FIG. 8a shows a calibrating element 2. The calibrating element has eight markers 3 which are arranged in a fixed spatial ratio to one another (possibly by a rigid connecting frame, as indicated by lines in FIG. 8a). The spatial arrangements shown in FIG. 8a is particularly advantageous: four of the markers 3 are arranged in a planar fashion in a first plane (lower plane) in a first rectangle arrangement and four further markers 3 are arranged in a planar manner in a second plane (upper plane) in a second rectangle arrangement, where the second rectangle arrangement defines a smaller rectangle surface than the first rectangle arrangement. The first and the second planes are arranged parallel to one another and the two rectangle arrangements are arranged about a common central axis perpendicular to the first and second plane.

The markers 3 emit radiation which can be detected both by the optical image sensor 70 and also by the nuclear radiation detector 40. The markers 3 can also reflect optical radiation in a further embodiment. This radiation can be approximately idealized by a point radiation source in embodiments. The signals of the eight markers 3 are therefore detected by the nuclear radiation detector 40 and by the image sensor 70 and transmitted to the calibrating module 90. FIG. 8b shows an image of the calibrating element 2 with the markers 3 recorded by the nuclear radiation detector 40 or by the image sensor 70. The markers 3 can, but need not be point radiation sources. In another embodiment, the markers 3 can therefore also be configured as lines, patterns or surfaces etc.

The calibrating module 90 has an image evaluating function which determines the respective image coordinates of the eight markers 3 (see FIG. 8b) in the nuclear radiation image detected by the nuclear radiation detector 40 and in the optical image detected by the image sensor 70. As a result, an assignment of at least these image coordinates is possible. As a result of these image coordinates, the remaining image coordinates of the nuclear radiation image and the optical image can be assigned by interpolation. The positions of three markers are actually already sufficient for the assignment. The problem of the assignment is overdetermined by the overall eight markers. This additional overdetermined information can then be used by means of a suitable interpolation algorithm for error correction and to achieve a more reliable assignment. Also a plurality of recordings of the calibrating elements 2 possibly in different orientations can be used in a similar manner in order to obtain a more robust and more reliable assignment of spatially the same image coordinates of the nuclear radiation image and the optical image. This calibration is made possible as a result of the imaging properties of the reference image acquisition module described above. The three-dimensionally arranged markers 3 can only be calibrated consistently thanks to the particular imaging properties described above—namely the fact that the optical radiation coming from the respective one of the nuclear partial fields of view is deflected substantially precisely to the respectively assigned one of the image areas. Formally this is manifest in that the overdetermined system of equations for assignment of the image coordinates can be solved (or that unsolvable equations of the system of equations which nevertheless exist must be based on inaccuracies and therefore can be compensated).

The calibrating module also allows manual operation. Here the two images, the optical image and the nuclear radiation image, are superposed as partial images and can be moved manually with respect to one another and distorted until all the marker positions overlap with sufficient accuracy.

In a further embodiment the calibrating element 2 can also be used for positioning the reference image acquisition module 60 or elements of the same relative to elements of the nuclear image acquisition module 30 (see, e.g. FIG. 2). For example, the image sensor 70 or the mirror 82 can be positioned such until all the markers 3 overlap with sufficient accuracy. This calibration can be accomplished manually or be included in a position calibrating routine of the calibrating module which outputs appropriate instructions for the positioning of elements of the reference image acquisition module 60 relative to elements of the nuclear image acquisition module 30.

A superposition module 92 is further shown in FIG. 7a. The superposition module 92 receives the image information from the nuclear radiation detector 40 and the image sensor 70 and receives assignment information from the calibrating module 90. By means of this information the superposition module 92 superposes the nuclear radiation image (first partial image) with the optical image (second partial image) to give a common superposed image in which images areas of the respective partial images spatially assigned to one another are superposed with one another. The superposition module 92 then outputs the superposed image to an image display 98. The respective image component of the partial images can then be set or fixedly predefined by a regulator. The superposition module 92 can also be switched between the output of both partial images in order to output either the one or the other partial image or optionally a superposed image. An advantage of the embodiment lies in that a calibration is only required if changes are made to the nuclear image acquisition module and/or to the reference image acquisition module. In the absence of such changes, the device can be used immediately and without further calibration.

Figure 9:
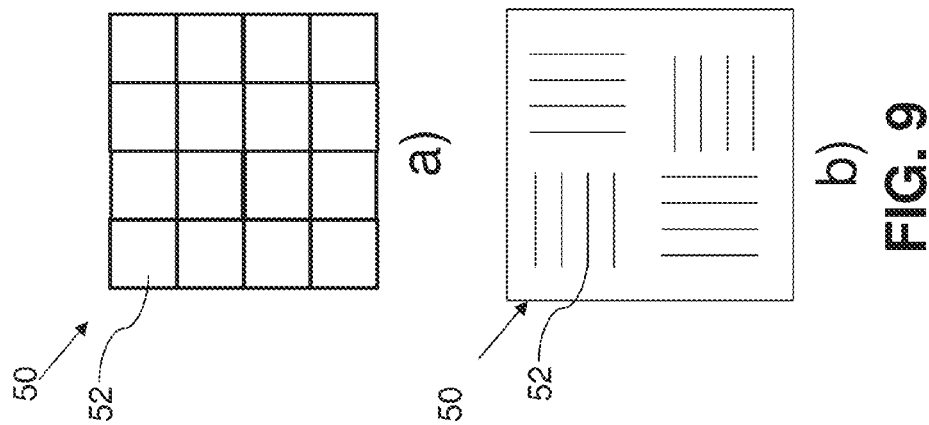
FIGS. 9a and 9b show various collimator openings in frontal view.

FIGS. 9a and 9b show various shapes of the collimator openings of the collimator 50 as an example in frontal view (in FIG. 1 when viewed from the direction of the nuclear field of view 36, i.e. from the left). These collimator openings can be arranged to be diverging or parallel. FIG. 9a shows an arrangement as a regular square matrix of image elements which leads to a pixel-like image. In FIG. 9b the collimator openings 50 each have an elongate shape and extend in various directions. As a result, in particular anisotropic structures can be clearly identified. The collimator 50 of FIG. 9b can be rotatable. Also a different, honeycomb-like arrangement of hexagonal collimator openings is possible.

The reference image acquisition module is adapted in corresponding manner to the shape of the collimator openings so that corresponding image areas are defined on the image sensor onto which the optical radiation coming from the respective nuclear partial fields of view is deflected. In the case where the image sensor is a pixel sensor, only the assignment of the individual pixels of the pixel sensor to the respective image areas assigned to the collimator openings differs. Alternatively the reference image acquisition module can, for example, also be equipped with an optical collimator. In this case, the optical collimator can be configured according to the collimator 50.

Subsequently some further general aspects of embodiments are described which can be combined with any embodiments described herein. According to one aspect, the optical image sensor is a pixel sensor and the image area is a pixel area. According to a further aspect, the reference field of view substantially completely contains the nuclear field of view. According to a further aspect, a respective image area on the image sensor is assigned to several of the nuclear partial fields of view or even to each of the nuclear partial fields of view.

According to a further aspect, the nuclear radiation detector is, for example, a gamma, beta, Compton camera and/or a PET detector. According to a further aspect, the nuclear radiation detector comprises a collimator, a scintillator and a photodiode array or equivalent nuclear radiation detector arrangements such as, for example, semiconductor detectors for direct detection of radiation, scintillators with connected photomultiplier tubes (PMT), scintillators with connected silicon photomultipliers (SiPM) etc. According to a further aspect, the nuclear image acquisition module has two nuclear radiation detectors located opposite one another for detecting positron emitters.

According to a further aspect, the collimator is a diverging holes collimator and the optical imaging system is focussing. According to a further aspect, the collimator is a parallel-hole collimator and the optical imaging system is substantially telecentric, that is for example comprises a telecentric lens arrangement or parallel-hole collimator. Herein an only approximately telecentric lens is considered to be telecentric; telecentric can also mean that a perspective centre of the lens arrangement does not lie at infinity but is merely more than five times, but preferably more than ten times further from the mirror than the optical image sensor. According to a further aspect, the collimator is a multipinhole collimator, a converging holes collimator, a slanting holes collimator or an aperture-coded collimator and the optical system is configured to have appropriate imaging properties (e.g. by using an appropriate collimator).

According to a further aspect, the nuclear image acquisition module defines a perspective nuclear radiation centre for the nuclear radiation and the reference image acquisition module defines a virtual perspective optical centre for the optical radiation wherein the nuclear radiation centre and the virtual optical centre are arranged at substantially the same position, i.e. within the limits of usual accuracy.

According to a further aspect, the image sensor is a first image sensor and the mirror is a first mirror and the reference image acquisition module has a second optical image sensor and a second mirror for deflecting the optical radiation from the reference field of view to the second image sensor. According to a further aspect, the mirrors are arranged so that a first part of the optical radiation is deflected by the first mirror onto the first image sensor and a second part of the optical radiation is deflected by the second mirror onto the second image sensor. According to a further aspect, the nuclear radiation detector and the image sensor are arranged on the same side of the reference field of view.

According to a further aspect, the device has a rigid frame which rigidly interconnects the optical image sensor and nuclear radiation detector (during use) but, for example, can contain calibrating screws or other movable elements outside the actual use. According to a further aspect, the device is adapted to output superposed images as real time images and/or moving images.

According to a further aspect, the device further comprises a calibrating module for assigning spatially congruent image coordinates of a nuclear radiation image detected by the nuclear radiation detector and an optical image detected by the image sensor. According to a further aspect, the device further comprises a superposition module for superposing the nuclear radiation image and the optical image to form a joint superposed image. According to a further aspect, the device further comprises an imaging system for spatial imaging, for reconstruction of a three-dimensional reconstruction image from nuclear image data, possibly by means of known methods for 3D image reconstruction and for saving the three-dimensional reconstruction image in an image memory. In particular, the nuclear image data can comprise data generated by the nuclear sensor. According to a further aspect, the device comprises a virtual image generation system for generating a virtual perspective image from data stored in the image memory so that the virtual perspective image has the same perspective as the optical image. According to a further aspect, the virtual image generation system is programmed to assign the virtual image and the optical image to one another possibly by means of assignment of optical markers contained in the optical image. According to a further aspect, the virtual image is a nuclear image.

According to a further aspect, the device comprises an image display. According to a further aspect, the device is a medical imaging device for determining a tracer concentration in the body of a living being, e.g. a human.

The invention claimed is:

1. A device for combined optical and nuclear image acquisition, comprising:
    a nuclear image acquisition module; and
    a reference image acquisition module, wherein:
        the nuclear image acquisition module is for detecting an intensity distribution of nuclear radiation coming from a nuclear field of view and comprises:
            a nuclear radiation detector, and
            a collimator arranged between the nuclear field of view and the nuclear radiation detector having a plurality of collimator openings, wherein the collimator openings are arranged for transmission of partial radiation of the nuclear radiation coming from a respective nuclear partial field of view of the nuclear field of view, and wherein:
        the reference image acquisition module is for detecting an intensity distribution of optical radiation coming from a reference field of view and comprises:
            an optical image sensor; and
            an optical imaging system for deflecting the optical radiation from the reference field of view to the image sensor, wherein the optical imaging system comprises a mirror for the optical radiation arranged between the reference field of view and the optical image sensor, wherein:
                on the image sensor a respective image area is assigned to at least one of the nuclear partial fields of view; and wherein:
                the optical imaging system is arranged to deflect the optical radiation coming from the at least one of the respective nuclear partial fields of view substantially exactly to the respectively assigned one of the image areas.

2. The device according to claim 1, wherein the optical image sensor is a pixel sensor and wherein the image area is a pixel area.

3. The device according to claim 1, wherein the reference field of view completely contains the nuclear field of view and wherein a respective image area on the image sensor is assigned to each of the nuclear partial fields of view.

4. The device according to claim 1, wherein the nuclear radiation detector is selected from the group consisting of gamma, beta, Compton camera, and PET detector.

5. The device according to claim 1, wherein the collimator is a diverging holes collimator and the optical imaging system is focussing, or wherein the collimator is a parallel-hole collimator and the optical imaging system is substantially telecentric.

6. The device according to claim 1, wherein the nuclear image acquisition module defines a perspective nuclear radiation centre for the nuclear radiation and the reference image acquisition module defines a virtual perspective optical centre for the optical radiation and wherein the nuclear radiation centre and the virtual optical centre are arranged at substantially the same position.

7. The device according to claim 1, further comprising a rigid frame which rigidly interconnects the optical image sensor and nuclear radiation detector.

8. The device according to claim 1, further comprising a calibrating module for assigning spatially congruent image coordinates of a nuclear radiation image detected by the nuclear radiation detector and an optical image detected by the image sensor.

9. The device according to claim 8, further comprising a superposition module for superposing the nuclear radiation image and the optical image to form a joint superposed image.

10. The device according to claim 1, wherein the optical image sensor is selected from the list comprising CCD digital camera, CMOS digital camera, multispectral camera, narrow-band camera, fluorescence camera, interference camera and time-of-flight camera.

11. Method for image acquisition, comprising
    (a) detecting an intensity distribution of nuclear radiation coming from a nuclear field of view by a nuclear image acquisition module, which nuclear image acquisition module comprises a nuclear radiation detector and a collimator having a plurality of collimator openings, wherein:
        partial radiation of the nuclear radiation coming from a respective nuclear partial field of view of the nuclear field of view is transmitted by a respective one of the collimator openings and then detected by a nuclear radiation detector;
    (b) deflecting, by an optical imaging system, optical radiation coming from a reference field of view to an optical image sensor on which image sensor a respective image area is assigned to at least one of the nuclear partial fields of view, wherein:
        a mirror of the optical imaging system deflects the optical radiation so that the optical radiation coming from a respective one of the nuclear partial fields of view is deflected substantially exactly to the respectively assigned one of the image areas; and
    (c) detecting an intensity distribution of the optical radiation deflected to the image sensor by an optical image sensor of the reference image acquisition module.

12. The method according to claim 11, further comprising assigning spatially congruent image coordinates of a nuclear radiation image detected by the nuclear radiation detector and an optical image detected by the image sensor by means of a calibration module.

13. The method according to claim 12, further comprising superposing the nuclear radiation image as a first partial image and the optical image as a second partial image to form a common superposed image in which image areas of the respective partial images spatially assigned to one another are superposed with one another, by means of a superposition module.

* * * * *